United States Patent [19]

Eichhorn et al.

[11] Patent Number: 5,776,652
[45] Date of Patent: Jul. 7, 1998

[54] AROMATIC HEXAFLUOROPROPANESULFONATE DIAZONIUM SALTS AND THEIR USE IN RADIATION-SENSITIVE MIXTURES

[75] Inventors: Mathias Eichhorn, Niedernhausen; Gerhard Buhr, Koenigstein, both of Germany

[73] Assignee: Agfa-Gevaert AG, Leverkusen, Germany

[21] Appl. No.: 949,777

[22] Filed: Oct. 14, 1997

Related U.S. Application Data

[63] Continuation of Ser. No. 430,070, Apr. 27, 1995, abandoned.

[30] Foreign Application Priority Data

Apr. 28, 1994 [DE] Germany ............... 44 14 897.6

[51] Int. Cl.[6] ................ G03F 7/021; G03F 7/023
[52] U.S. Cl. ............... 430/163; 430/165; 430/176; 430/191; 430/192
[58] Field of Search ................ 430/176, 191, 430/192, 157, 163, 165, 270.1

[56] References Cited

U.S. PATENT DOCUMENTS

| 3,679,419 | 7/1972 | Gillich. | |
|---|---|---|---|
| 3,849,392 | 11/1974 | Steppan. | |
| 4,101,323 | 7/1978 | Buhr et al. | 430/176 |
| 4,163,672 | 8/1979 | Stahlhofen | 430/176 |
| 4,247,611 | 1/1981 | Sander et al. | 430/286 |
| 4,889,789 | 12/1989 | Stahlhofen | 430/191 |
| 5,286,602 | 2/1994 | Pawlowski et al. | 430/270 |
| 5,326,840 | 7/1994 | Przybilla et al. | 430/270.1 |

FOREIGN PATENT DOCUMENTS

| 0102450 | 3/1984 | European Pat. Off. . |
| 0263434 | 4/1988 | European Pat. Off. . |
| 0353600 | 2/1990 | European Pat. Off. . |
| 530815 | 3/1993 | European Pat. Off. . |
| 1154749 | 6/1969 | United Kingdom . |

*Primary Examiner*—Christopher G. Young
*Attorney, Agent, or Firm*—Foley & Lardner

[57] ABSTRACT

The invention relates to aromatic or heteroaromatic mono- or bis-diazonium 1,1,2,3,3,3-hexafluoro-propanesulfonates. They are employed in positive-working or negative-working radiation-sensitive mixtures which are used for coating radiation-sensitive recording material.

22 Claims, No Drawings

AROMATIC HEXAFLUOROPROPANESULFONATE DIAZONIUM SALTS AND THEIR USE IN RADIATION-SENSITIVE MIXTURES

This application is a continuation application of Ser. No. 08/430,070, filed Apr. 27, 1995 now abandoned.

BACKGROUND OF THE INVENTION

Field of the Invention

The invention relates to aromatic diazonium compounds and a method of preparing them and also to a radiation-sensitive mixture which contains a) a compound which forms acid on exposure to actinic radiation, $b^1$) for a positive-working mixture, a compound whose solubility in aqueous alkaline solution increases on exposure to the radiation or the acid, or $b^2$) for a negative-working mixture, a compound whose solubility in aqueous alkaline solution decreases on exposure to said acid, and optionally c) a polymeric organic binder which is insoluble in water but soluble, or at least swellable, in aqueous alkaline solution.

In addition, the invention relates to a recording material having a base and a radiation-sensitive coating.

Aromatic diazonium salts have been known for a long time. Thus, DE-A 20 24 242 (=U.S. Pat. No. 3,849,392) describes a number of diazonium salts. Specifically, it discloses, in particular, 4-anilinobenzenediazonium, 4-anilino-2-methoxybenzenediazonium, 4-(4-methoxyanilino)benzenediazonium, 4-(2-carboxyanilino)benzenediazonium, 2,5-diethoxy-4-(4-ethoxyanilino)benzenediazonium, 2,5-dimethoxy-4-p-tolylmercaptobenzenediazonium, 2,5-dimethoxy-4-phenoxybenzenediazonium, 4-(2,5-diethoxybenzoylamino)-2,5-diethoxybenzenediazonium, 3-methoxydibenzofuran-2-diazonium, 4-(methyl-1-naphthylmethylamino)benzenediazonium, 4-anilino-2-carboxybenzenediazonium, 2,5-dimethoxy-4-(N-methyl-N-phenylmercaptoacetylamino)-benzenediazonium and 4-[N-methyl-N-(2-phenylmercapto-ethyl)amino] benzenediazonium salts. All these salts are in the form of chlorides, sulfates or phosphates. Condensation products of these salts were used in radiation-sensitive mixtures.

DE-A 26 41 099 (=U.S. Pat. No. 4,163,672) discloses photosensitive 2,4,5-trisubstituted benzenediazonium salts which cleave acid on irradiation. These salts take the form hexafluorophosphates, tetrafluoroborates or hexafluoroarsenates. They were used in a photosensitive mixture which, in addition to one of these salts, contains esters or amides of an (o-naphthoquinone diazide) sulfonic acid or (o-naphthoquinone diazide) carboxylic acid and a triphenylmethane, azine or anthraquinone dyestuff which is capable of salt formation.

The so-called "chemically enhanced" mixtures are particularly photosensitive. They generally contain a compound which, on exposure to radiation, releases a catalytically active agent (usually an acid) and a compound b) which is altered by the catalytic action of said agent in such a way that its solubility in a developer increases or decreases. In positive-working mixtures, this last-mentioned compound is converted into more readily soluble cleavage products, whereas, in negative-working mixtures, it is normally converted into more sparingly soluble, crosslinked products. Numerous compounds are already known which release catalytically active acid on irradiation. These "photostarters" include triazines which are substituted with trihalomethyl groups. On irradiation, they release hydrohalic acids. However, hydrohalic acids are relatively volatile, with the result that they frequently diffuse out of the copying coating and consequently do not develop the full catalytic effectiveness. The strong nucleophilic nature of the halide anion has the result, in addition, that an appreciable portion of the acid is consumed by undesirable side reactions.

EP-A 0 102 450 describes a chemically enhanced photosensitive mixture in which aryldiazonium, triarylsulfonium or diaryliodonium salts are used as photostarters. These salts take the form of tetrafluoroborates, hexafluoroantimonates or hexafluorophosphates. The acids liberated from these salts on irradiation are less volatile than hydrohalic acids and the associated anion is also less nucleophilic. However, the metal component is a disadvantage. If a semiconductor substrate is coated with a mixture containing such a salt, an undesirable doping of the substrate with said metals may occur.

EP-A 0 353 600 describes aromatic diazonium salts whose anion does not contain such metals. These salts take the form of methanesulfonates, trifluoromethanesulfonates or trifluoroacetates. However, they are insufficiently soluble in many of the solvents commonly used for photosensitive mixtures. A further disadvantage is the high tendency of these salts to crystallize.

SUMMARY OF THE INVENTION

An object of the invention is to provide diazonium salts which are suitable as photostarters without at the same time having the disadvantages described in the prior art. In addition, such diazonium salts should have as low a toxicity as possible. The object is achieved by aromatic and heteroaromatic mono- or bisdiazonium 1,1,2,3,3,3-hexafluoropropane sulfonates.

It is also an object of the present invention to provide a positive-working or negative working radiation-sensitive mixture which comprises the inventive aromatic and heteraromatic diazonium salts for coating radiation-sensitive recording materials.

In accordance with another aspect of the present invention, there is provided a recording material having a base that is coated with the inventive radiation-sensitive mixture.

Further objects, features and advantages of the present invention will become apparent from the detailed description of the preferred embodiments that follows.

DETAILED DESCRIPTION OF PREFERRED EMBODIMENTS

A feature of the aromatice and heteraromatic mono- or bisdiazonium 1,1,2,3,3,3-hexafluoropropane sulfonates is that the aromatic or heteroaromatic cation generally contains 4 to 20 carbon atoms. The heteroatoms in the heteroaromatic compounds are preferably oxygen, sulfur and/or nitrogen.

Of the aromatic diazonium 1,1,2,3,3,3-hexafluoropropane-sulfonates, optionally substituted benzenediazonium 1,1,2,3,3,3-hexafluoropropanesulfonates and fluorene-diazonium 1,1,2,3,3,3-hexafluoropropanesulfonates are preferred. The substituents optionally present are preferably halogen atoms, or hydroxyl, ($C_1$–$C_4$)alkoxy, phenoxy, ($C_1$–$C_4$)alkyl, amino, ($C_1$–$C_4$)alkylamino, di($C_1$–$C_4$)alkylamino, ($C_1$–$C_4$)hydroxyalkylamino, di ($C_1$–$C_4$)hydroxyalkylamino, ($C_1$–$C_4$)hydroxyalkyl($C_1$–$C_4$)alkylamino, pyrrolidino, piperidino, morpholino, phenylamino, nitro, phenyl or phenylazo groups. They may also be benzoyl groups which are optionally substituted in addition with a ($C_1$–$C_4$)alkyl, ($C_1$–$C_4$)alkoxy or diazonium group. Finally, the substituents optionally present may also be phenylmercapto groups, which are likewise optionally substituted in addition with a ($C_1$–$C_4$)alkyl or ($C_1$–$C_4$)alkoxy group.

Of the heteroaromatic diazonium 1,1,2,3,3,3-hexafluoropropanesulfonates, di-benzofuran-x-diazonium 1,1,2,3,3,3-hexafluoropropanesulfonates, di-x-benzo[b,d]thiophenediazonium 1,1,2,3,3,3-hexafluoropropanesulfonates, 9-($C_1$–$C_4$)alkyl-carbazole-x-diazonium 1,1,2,3,3,3-hexafluoropropanesulfonates are preferred, where x specifies the position number. The diazonium group may generally be at any of the positions 1 to 8 of the heterocycles mentioned.

The diazonium salts of 1,1,2,3,3,3-hexafluoropropanesulfonic acid (=HFPSA) according to the invention can be prepared by processes which are known per se to the person skilled in the art. For example, they can be prepared from the corresponding (hetero)aromatic diazonium halides or sulfates by reaction with HFPSA (method A) or by diazotization of a (hetero)aromatic amine in the presence of HFPSA (method B).

In the case of method A, the diazonium halide or sulfate, which is in solution, is generally reacted with HFPSA while stirring. In this case, the solvent is expediently chosen so that the diazonium 1,1,2,3,3,3-hexafluoropropanesulfonate formed in the process precipitates as a solid and can be separated. One solvent which fulfils these requirements in many cases is water. In other cases, organic solvents such as ethers, ketones or alcohols may be more advantageous.

The diazotization of aromatic amines in the presence of strong acids has been known for a long time. It is normally carried out in aqueous solution using sodium nitrite, the diazonium salts produced remaining at least partly dissolved. In the preparation of the diazonium salts according to the invention, the corresponding (hetero)arylamines are advantageously diazotized in organic solvents using isoamyl nitrite. In this process, the diazonium 1,1,2,3,3,3-hexafluoropropanesulfonates precipitate in a finely divided form which can readily be isolated. Only in exceptional cases is it necessary also to add a precipitating agent beforehand.

The radiation-sensitive mixture according to the invention which contains a) a compound which forms acid on exposure to actinic radiation, $b^1$) for a positive-working mixture, a compound whose solubility in aqueous alkaline solution increases on exposure to the radiation or the acid, or $b^2$) for a negative-working mixture, a compound whose solubility in aqueous alkaline solution decreases on exposure to the acid, and optionally c) a polymeric organic binder which is insoluble in water but soluble, or at least swellable, in aqueous alkaline solution is one wherein the compound a) is an aromatic or heteroaromatic diazonium salt of 1,1,2,3,3,3-hexafluoropropanesulfonic acid. Preferred aromatic or heteroaromatic diazonium salts are specified above.

The compound $b^1$), whose solubility in aqueous alkaline solution increases on exposure to the acid, is preferably a polymer containing acid-labile groups. Preferred in this connection are polymers which have at least one acid-cleavable C—O—C bond. These include polymers in which aromatic rings are substituted with acid-cleavable tert-butoxycarbonyloxy, tert-butoxycarbonyl or tert-butoxy groups. Particularly preferred compounds $b^1$) are optionally substituted, in particular alkyl-substituted, polyhydroxystyrenes whose phenolic hydroxyl groups are completely or partly replaced by tert-butoxycarbonyloxy, tert-butoxycarbonyl or tert-butoxy groups.

Such polymers are obtained, for example, from polyhydroxystyrenes or novolaks by partial or complete reaction with di-tert-butyl dicarbonate. Also particularly suitable are polymers containing groups comprising tert-butyl methacrylate. They furthermore include acetals and ketals containing acid-cleavable C—O—C bonds.

Suitable low-molecular-weight acetals and ketals are described in DE-A 26 10 842 (=U.S. Pat. No. 4,101,323), and suitable polymeric acetals and ketals are described in DE-A 27 18 254 (=U.S. Pat. No. 4,247,611). Furthermore, poly(N,O-acetals) such as those described in EP-A 0 510 449 (=U.S. Pat. No. 5,286,602) are also suitable. The proportion of these acid-labile polymers is approximately 60 to 99 percent by weight, based on the total weight of the nonvolatile constituents of the mixture, i.e., the constituents of the solid photosensitive coating obtained after evaporation of the solvent. The amount relates to a mixture not containing one of the polymeric binders c). If the polymeric acid-cleavable compounds mentioned are used, the polymeric binder c) is not absolutely necessary. If, however, one of these binders is used, the proportion of the acid-labile polymers decreases accordingly.

The compound $b^1$), whose solubility in aqueous alkaline solution increases on exposure to actinic radiation, is preferably an o-quinone diazide, particularly preferably an o-naphthoquinone diazide. Particularly suitable o-naphthoquinone diazides are optionally still further substituted bis[4-(1,2-naphthoquinone 2-diazide-4- or -5-sulfonyloxy)phenyl]-($C_2$–$C_9$) alkanoic acids and their esters, 2,3,4,2',3',4'-hexakis(1,2-naphthoquinone 2-diazide-4- or -5-sulfonyloxy)-5,5'-dialkanoyl- or -diaroyldiphenylmethanes and optionally still further substituted bis[4,4'-(1,2-naphthoquinone 2-diazide-4- or -5-sulfonyloxy)benzoyl]-($C_2$–$C_{18}$)alkanes. Esters of (1,2-naphthoquinone 2-diazide)-4- or -5-sulfonic acid and compounds containing phenolic hydroxyl groups, in particular those containing 2 to 6 phenolic hydroxyl groups are generally suitable. In such mixtures, the diazonium salts according to the invention have the function of a contrast former. The particular advantage is that the thermal stability of latent images formed from recording materials produced with said mixture is markedly increased. As a comparison, recording materials were used whose radiation-sensitive coating contains other radiation-sensitive contrast formers such as (1,2-naphthoquinone 2-diazide)-4-sulfonyl chloride or substituted trihalomethyl-s-triazines.

The compound $b^2$), whose solubility in aqueous alkaline solution decreases on exposure to the acid, preferably contains at least two acid-crosslinkable groups, in particular at least two hydroxymethyl, methoxymethyl or acetoxymethyl groups. These include compounds of the formulae ($R^1$O—CHR$^3$)$_n$-A-(CHR$^3$—OR$^2$)$_m$ and ($R^1$O—CHR$^3$)$_n$-A-Y-A-(CHR$^3$—OR$^2$)$_m$ in which A is an optionally substituted mononuclear aromatic hydrocarbon or an oxygen-, sulfur- or nitrogen-containing heterocyclic aromatic compound, Y is a single bond, ($C_1$–$C_4$)alkylene or ($C_1$–$C_4$) alkylenedioxy, in which carbon chains may be interrupted by oxygen atoms, —O—, —S—, —SO$_2$—, —CO—, —CO—O—, —O—CO—O—, —CO—NH— or phenylene-dioxy, $R^1$ and $R^2$ are identical or different and are hydrogen atoms, or ($C_1$–$C_4$)alkyl, cycloalkyl, optionally substituted aryl, aralkyl or alkanoyl groups, $R^3$ is a hydrogen atom, or a $(C_1-C_4)$alkyl or an optionally substituted phenyl group, n is an integer from 1 to 3 and m is an integer from 0 to 3, provided that n+m is at least 2.

Hexa-N-methoxymethylmelamine, uncured alkyl-etherified melamine/formaldehyde resins having a mean molecular weight $M_w$ of 500 to 1,500 (EP-A 0 263 434) and urea/formaldehyde or urea/formaldehyde condensation products (EP-A 0 285 013) are also suitable as cross-linkers.

In general, the proportion of the diazonium salts according to the invention is from about 1 to about 40 percent by weight, preferably 2 to 25 percent by weight, based in each case on the total weight of the nonvolatile constituents of the mixture. If the mixture contains one of the abovementioned compounds whose solubility in aqueous alkaline developers increases under the influence of radiation, the proportion of the diazonium salts according to the invention is somewhat lower. It is then preferably 0.5 to 20 percent by weight, particularly preferably 1 to 10 percent by weight, again based on the total weight of the nonvolatile constituents of the mixture.

If one of the acid-cleavable ($b^1$) or acid-crosslinkable compounds ($b^2$) is of low molecular weight, the mixture expediently contains a polymeric binder c) in addition. Polymers containing phenolic hydroxyl groups or carboxyl groups are suitable. These include phenolic resins, in particular poly(4-hydroxystyrene), cresol/formaldehyde novolaks (melting range 105° to 120° C. according to DIN 53 181) and phenol/formaldehyde novolaks (melting range 110° to 120° C. according to DIN 53 181). Copolymers of methacrylic acid/methylmethacrylate, crotonic acid/vinyl acetate and maleic anhydride/styrene can also be used. In the case of the maleic anhydride/styrene copolymers, the carboxyl groups are first formed by alkaline saponification of the anhydride groups. The mixture may contain various binders at the same time.

The proportion of the binder c) is generally 30 to 90 percent by weight, preferably 55 to 85 percent by weight, based in all cases on the total weight of the nonvolatile constituents of the mixture.

In addition to the constituents mentioned, the mixture according to the invention may also contain up to approximately 20 percent by weight, based on the total weight of the nonvolatile constituents of the mixture, of other homopolymers or copolymers. These are, in particular, vinyl polymers such as polyvinyl acetates, polyacrylates and polyvinylethers which may be modified by the incorporation of comonomers. The development characteristics can be influenced by these additional polymers.

In order to influence certain characteristics such as flexibility, adhesion, gloss, UV absorption etc., the mixture according to the invention may, depending on the application, furthermore contain minor amounts of polyglycols, cellulose derivatives, such as ethylcellulose, wetting agents, UV absorbers, dyes and finely divided pigments. The triphenylmethane dyes, in particular in the form of their carbinol bases have proved advantageous as dyestuffs.

Finally, the present invention also relates to a recording material having a base and a radiation-sensitive coating, wherein the coating is composed of the radiation-sensitive mixture according to the invention.

The recording material is prepared by applying a solution of the mixture according to the invention to the base and then removing the solvent. Suitable as solvents are ketones (such as butanone), chlorinated hydrocarbons (trichloroethylene and 1,1,1-trichloroethane), alcohols (such as propanol), ethers (such as tetrahydrofuran), glycol monoalkyl ethers (such as ethylene glycol monoethyl ether and propylene glycol monomethyl ether), glycol monoalkyl ether acetates (such as propylene glycol monomethyl ether acetate) and esters (such as butyl acetate). Mixtures of these may also be used. Acetonitrile, dioxane or dimethylformamide may furthermore be present as an additional solvent. Generally, all those solvents can be used which do not react in an undesirable way with the constituents of the mixture according to the invention or with the base material.

Solvents and solids content of the solution also depend on the coating and drying processes. Coatings of up to approximately 5 μm thickness are generally spun on or applied with a doctor blade and then dried. The solutions used in these processes have a solids content of up to approximately 40 percent by weight. If the base material is to be coated on both sides, it is immersed in a suitable solution. Low-boiling solvents, which are consequently easy to remove, allow the coating to dry rapidly. The coating may also be applied by spraying-on or by application with the aid of rollers or flat-film dies. Single plates, in particular those composed of zinc or multimetal, are advantageously coated by casting application (curtain coating).

To produce offset printing plates, the recording materials usually have a base composed of mechanically and/or electrochemically grained and optionally anodized aluminum, which may furthermore be pretreated chemically, for example with polyvinylphosphonic acid, silicates or phosphates. Multimetal plates having a Cu/Cr or brass/Cr surface are also suitable. The recording coatings applied thereto are usually thinner than 10 μm.

Coatings having a thickness of more than 10 μm are usually first applied to a temporary base (normally a plastics sheet) and transferred to the final base therefrom. The plastics sheet is frequently a polyester film (for example, poly(ethylene terephthalate)) or a polyolefin sheet (for example, polypropylene).

Zinc or magnesium bases and their commercial microcrystalline alloys for single-stage etching processes or etchable plastics such as polyoxymethylene are used to produce letterpress plates.

Suitable for gravure printing forms and screen-printing forms are bases having copper or nickel surfaces, to which the mixture according to the invention adheres particularly well. These coatings are also remarkable here for good etch resistance.

The mixtures according to the invention may furthermore be used as photoresists and in chemical milling. They are also suitable for the coating of printed circuit boards composed of an electrically non-conducting material which are provided with a copper cladding on one or both sides, glass or ceramic materials, optionally pretreated in an adhesion-promoting manner, silicon wafers on whose surface there is optionally a nitride coating or oxide coating; the coating may be carried out directly or with the aid of a temporary base;

wood, textiles and the surfaces of many materials which are provided with an image by projection and are resistant to the action of alkaline developers.

The standard equipment and conditions may be adopted for drying the coating, and temperatures around 100° C. and, for a short time, up to 120° C. are tolerated without loss of sensitivity to radiation.

The standard copying equipment such as tubular lamps, xenone pulsed lamps, metal-halide-doped mercury-vapor-pressure lamps and carbon-arc lamps can be used for the purpose of exposure. In addition, exposure in standard projection and enlargement equipment using light from metal-filament lamps and contact exposure using conventional incandescent lamps is possible. The exposure can also be carried out with the coherent light of a laser. Short-wave lasers of the correct power, for example argon ion lasers, krypton ion lasers, dye lasers, helium/cadmium lasers and also excimer lasers which emit between 193 and 633 nm are suitable. The laser beam is controlled by a preprogrammed line and/or raster movement.

In the case of the positive-working radiation-sensitive mixtures according to the invention, the imagewise exposed or irradiated coating can be removed, optionally after a thermal aftertreatment, with virtually the same developers as used for commercial naphthoquinone diazide coatings and resists. In the case of the negative-working radiation-sensitive mixtures according to the invention, on the other hand, the unexposed areas are removed by the developer. The copying conditions of the novel coatings may advantageously be adjusted to the known aids such as developers and programmed spray-development equipment. The aqueous developer solutions may contain, for example, alkali-metal phosphates, alkali-metal silicates or alkali-metal hydroxides and, furthermore, wetting agents and smaller proportions of organic solvents. In certain cases, solvent/water mixtures can also be used as developers. The most beneficial developer can be determined by experiments with the coating used in a particular case. If necessary, the development may be assisted mechanically. To increase the resistance during printing and the resistance to wash-out agents, deletion fluid and inks which can be cured by UV light, the developed plates may be heated for a short time at elevated temperatures, as is disclosed for diazo coatings in GB-A 1 154 749.

The diazonium 1,1,2,3,3,3-hexafluoropropanesulfonates according to the invention can be used not only in the radiation-sensitive mixtures described but wherever photosensitive diazonium salts have hitherto been used, for example to produce the microfilms and dyeline paper used in diazotype.

Examples of the preferred diazonium 1,1,2,3,3,3-hexafluoropropanesulfonates according to the invention and of their application in radiation-sensitive mixtures are given below without restricting the invention to these examples.

EXAMPLE 1

Synthesis of 2,5-diethoxy-4-p-tolylmercaptobenzenediazonium 1,1,2,3,3,3-hexafluoropropanesulfonate (method A)

50 g of 2,5-diethoxy-4-p-tolylmercaptobenzenediazonium chloride 1/2 $ZnCl_2$ were dissolved in 1.5 l of water. 20 ml of 1,1,2,3,3,3-hexafluoropropanesulfonic acid were then added dropwise to the filtered solution while stirring vigorously. The product, which precipitates as oily drops, solidified after a few minutes, was filtered off by suction, suspended in 1 l of water while stirring vigorously, again filtered off by suction and, finally, dried. 56.5 g of 2,5-diethoxy-4-p-tolylmercaptobenzenediazonium 1,1,2,3,3,3-hexafluoropropanesulfonate were obtained as a fine, light brown powder.

EXAMPLE 2

Synthesis of 9-ethyl-3-carbazolediazonium 1,1,2,3,3,3-hexafluoropropanesulfonate (method B)

3 ml of 1,1,2,3,3,3-hexafluoropropanesulfonic acid were added to a solution of 20 ml of tetrahydrofuran (THF) and 4.2 g of 9-ethyl-3-carbazolylamine. After cooling to 0° C., 3 ml of isoamyl nitrite were added dropwise while stirring in such a way that the temperature did not rise above 10° C. After completion of the dropwise addition, the icebath was removed and the stirring of the reaction mixture was continued for a further 4 h. 50 ml of diethyl ether were added, and the precipitate produced was filtered off by suction, washed with a little diethyl ether and dried. 7.4 g of 9-ethyl-3-carbazolediazonium 1,1,2,3,3,3-hexafluoropropanesulfonate was obtained as a yellow, finely crystalline powder.

EXAMPLES 3 TO 9

TABLE 1

| | Synthesized diazonium 1,2,3,3,3-hexafluoropropanesulfonates | | | |
|---|---|---|---|---|
| Ex. Graphic formula | Method | $\lambda_{max}$ [nm] | $\epsilon$ [l·mol$^{-1}$·cm$^{-1}$] | M.p. [°C.]* |
| 3 $H_3C-\bigcirc-S-\bigcirc(OC_2H_5)(C_2H_5O)-N_2^+X^-$ | A | 402 | 14470 | 86 |
| 4 (9-ethyl-carbazole-N$_2^+$X$^-$) | B | 381 | 12760 | 134 |

TABLE 1-continued

Synthesized diazonium 1,2,3,3,3-hexafluoro-propanesulfonates

| Ex. | Graphic formula | Method | $\lambda_{max}$ [nm] | $\epsilon$ [l·mol$^{-1}$·cm$^{-1}$] | M.p. [°C.]* |
|---|---|---|---|---|---|
| 5 | (fluorene-N$_2^+$X$^-$) | B | 364 | 22700 | 136 |
| 6 | (C$_6$H$_5$—N=N—C$_6$H$_4$—N$_2^+$X$^-$) | B | 315 | 18700 | 132 |
| 7 | (X$^-$N$_2^+$—C$_6$H$_4$—CO—C$_6$H$_4$—N$_2^+$X$^-$) | B | 282 | 8320 | 117 |
| 8 | (morpholino-2,5-dimethoxyphenyl-N$_2^+$X$^-$) | A | 400 | 15700 | 136 |
| 9 | (Cl—C$_6$H$_4$—O—C$_6$H$_3$(N(C$_2$H$_5$)$_2$)—N$_2^+$X$^-$) | A | 265 | 15080 | 93 |

X$^-$ = CF$_3$CHFCF$_2$SO$_3^-$
*In all cases, melting takes place with decomposition and evolution of gas.

EXAMPLLE 10 TO 19

The examples below illustrate the improved solubility of the diazonium 1,1,2,3,3,3-hexafluoropropanesulfonates according to the invention in the solvents preferably used for coating radiation-sensitive mixtures.

TABLE 2

Solubilities of diazonium 1,1,2,3,3,3-hexafluoropropanesulfonates and diazonium trifluoromethanesulfonates

| Ex. | Graphic formula | X$^-$ | Solubility [g/100 g] | | Note |
|---|---|---|---|---|---|
| | | | PGMEA* | FLG** | |
| 10 | (H$_3$C—C$_6$H$_4$—S—C$_6$H$_3$(OC$_2$H$_5$)—N$_2^+$X$^-$ with OC$_2$H$_5$) | CF$_3$SO$_3^-$ | 16.5 | 43 | PGMEA: incipient cryst · after 2 d |
| 11 | | CF$_3$CHFC$_2$SO$_3^-$ | >20 | >70 | PGMEA: no cryst · after 5 d |

TABLE 2-continued

Solubilities of diazonium 1,1,2,3,3,3-hexafluoropropanesulfonates and diazonium trifluoromethanesulfonates

| Ex. | Graphic formula | X⁻ | Solubility [g/100 g] PGMEA* | FLG** | Note |
|---|---|---|---|---|---|
| 12 | [carbazole with N–C₂H₅, N₂⁺X⁻] | CF₃SO₃⁻ | 0.07 | 0.5 | |
| 13 | | CF₃CHFCF₂SO₃⁻ | 0.60 | 4.5 | |
| 14 | [fluorene, N₂⁺X⁻] | CF₃SO₃⁻ | 0.33 | 1.2 | |
| 15 | | CF₃CHFCF₂SO₃⁻ | 0.35 | >2.0 | |
| 16 | [Ph–N=N–Ph–N₂⁺X⁻] | CF₃SO₃⁻ | 0.07 | 0.5 | |
| 17 | | CF₃CHFCF₂SO₃⁻ | 0.20 | >2.0 | |
| 18 | [X⁻N₂⁺–Ph–CO–Ph–N₂⁺X⁻] | CF₃SO₃⁻ | not tested | 1.7 | |
| 19 | | CF₃CHFCF₂SO₃⁻ | | 2.0 | |

*Propylene glycol monomethyl ether acetate
**Mixture of tetrahydrofuran and propylene glycol monomethyl ether in the volumetric ratio of 1:1

EXAMPLES 20–23

A plate made of electrochemically grained and anodized aluminum was spin-coated with a solution composed of

| 9.00 parts by weight of | a reaction product of polyhydroxystyrene and di-tert-butyl dicarbonate (OH number 267) |
| 0.50 parts by weight of | diazonium 1,1,2,3,3,3-hexafluoropropanesulfonate in accordance with Table 3, |
| 0.08 parts by weight of | crystal violet base and |
| 175 parts by weight of | butanone (methyl ethyl ketone) | and heated at 100° C. in a drying oven. After drying, the coating thickness was 1.9 μm. The plate was exposed through a half-tone step wedge having 13 steps with a density gradation of 0.15 under a 5 kW metal-halide lamp at a distance of 110 cm, afterheated for 1 min at 100° C. and developed in an aqueous alkaline developer of the composition

| 5.5 parts by weight of | sodium metasilicate.9 H₂O, |
| 3.4 parts by weight of | trisodium phosphate.12 H₂O, |
| 0.4 parts by weight of | anhydrous monosodium phosphate and |
| 90.7 parts by weight of | fully dimineralized water | for 30 s. In each case, a positive image of the printing artwork was obtained. Table 3 shows the exposure time for which step 3 of the half-tone wedge was reproduced on the plate in completely open form.

TABLE 3

| Example | Acid donor according to Tab. 1 | Exposure time in s |
|---|---|---|
| 20 | 3 | 12 |
| 21 | 4 | 60 |
| 22 | 5 | 25 |
| 23 | 8 | 40 |
| Comp.* | — | 75 |

*Standard positive printing plate (®)OZASOL P61

A plate in accordance with Example 20 was clamped in an offset printing press and yielded more than 100,000 good-quality impressions.

EXAMPLE 24

A plate made of electrochemically grained and anodized aluminum was spin-coated with a solution composed of

| 27.00 parts by weight of | a novolak resin ((®)Alnovol PN 429/430), |
| 8.00 parts by weight of | a polymeric ortho ester prepared by reacting trimethyl orthoformate and 2-ethyl-2-(4-hydroxybutoxymethyl)-1,3-propanediol, |
| 0.70 parts by weight of | diazonium 1,1,2,3,3,3-hexafluoropropanesulfonate in accordance with Table 1, Example 3, |
| 0.20 parts by weight of | crystal violet chloride and |
| 675 parts by weight of | butanone | and heated at 100° C. in a drying oven. After drying, the coating thickness was 1.9 μm. The plate was exposed through a half-tone step wedge having 13 steps with a density gradation of 0.15 under a 5 kW metal-halide lamp at a distance of 110 cm for 15 s and developed in an aqueous alkaline developer of the composition in accordance with Examples 20 to 23, diluted 1:1 with water, for 30 s. A positive image of the film artwork was obtained, step 3 of the half-tone step wedge used being reproduced on the plate in completely open form.

EXAMPLES 25–27

A plate made of electrochemically grained and anodized aluminum was spin-coated with a solution composed of

| | |
|---|---|
| 9.00 parts by weight of | a novolak resin ((R)Alnovol PN 429/430) |
| 2.00 parts by weight of | an esterification product of 1 mol of 2,3,4-trihydroxy-benzophenone and 3 mol of (1,2-naphthoquinone 2-diazide)-5-sulfonyl chloride, |
| 0.20 parts by weight of | crystal violet chloride and |
| 175 parts by weight of | butanone | to which the parts by weight listed in Table 4 of the various substances were added in each case as contrast formers, and heated at 100° C. in a drying oven. After drying, the coating thickness was 1.9 μm. The plates were half-covered with a black sheet which was opaque to light and exposed for 100 s in each case under a 5 kW metal-halide lamp at a distance of 110 cm. After the image contrast produced had been measured as the difference in the full-tone densities of the unexposed and exposed areas, the plates were aged at 100° C. and the decrease in the image contrast with time was observed. Table 4 shows the superior thermal stability of the image contrast when the diazoniurn 1,1,2,3,3,3-hexafluoropropanesulfonates according to the invention are used.

TABLE 4

| Ex. No. | Contrast former | Parts by weight | Image Zero Value | contrast 15 min | 4 h |
|---|---|---|---|---|---|
| 25 | (1,2-naphthoquinone 2-diazide)-4-sulfonyl chloride | 0.3 | 0.24 | 0.03 | — |
| 26 | 2-(4-stilbenyl)-4,6-bis-trichloromethyl-s-triazine | 0.1 | 0.25 | 0.02 | — |
| 27 | diazonium 1,1,2,3,-3,3-hexafluoropropane-sulfonate 3 in accordance with Table 1 | 0.45 | 0.29 | 0.28 | 0.25 |

EXAMPLE 28

A 125 μm thick polyethylene terephthalate) sheet having an adhesion-promoting coating was coated with a solution composed of

| | |
|---|---|
| 67.5 parts by weight of | acetone, |
| 17.5 parts by weight of | methanol, |
| 4.0 parts by weight of | n-butanol, |
| 4.0 parts by weight of | ethylene glycol monomethyl ether, |
| 7.0 parts by weight of | cellulose acetate propionate, |
| 0.2 parts by weight of | 5-sulfosalicylic acid, |
| 0.1 parts by weight of | 2,4-dihydroxybenzoic acid, |
| 1.7 parts by weight of | diazonium hexafluoropropane-sulfonate in accordance with Table 1, Example 9, and |
| 1.0 parts by weight of | 2,2'-dimethyl-4,4'-di-hydroxy-5,5'-di-tert-butyl-diphenyl sulfide | and dried for 1 min at 90° C. in a circulating-air drying oven. After drying, the coating weight was 8 g/m². The duplicating film obtained was exposed through a transparent lineart and developed in moist ammonia gas. A positive copy of the film artwork was obtained which had orange-red lines on a transparent background.

What is claimed is:

1. A radiation-sensitive mixture which contains
    a) a compound which forms acid on exposure to actinic radiation,
    b¹) for a positive-working mixture, a compound whose solubility in aqueous alkaline solution increases on exposure to the radiation or the acid, or
    b²) for a negative-working mixture, a compound whose solubility in aqueous alkaline solution decreases on exposure to the acid,
    c) wherein the compound a) is an aromatic or heteroaromaticmono- or bisdiazonium 1,1,2,3,3,3-hexafluoropropanesulfonate.

2. The radiation-sensitive mixture as claimed in claim 23, wherein the compound a) is a benzenediazonium 1,1,2,3,3, 3-hexafluoropropanesulfonate or a fluorenediazonium 1,1,2, 3,3,3-hexafluoropropanesulfonate.

3. The radiation-sensitive mixture as claimed in claim 2, wherein the compound a) is substituted with one or more of halogen atoms, or hydroxyl, ($C_1$–$C_4$) alkoxy, phenoxy, ($C_1$–$C_4$) alkyl, amino, ($C_1$–$C_4$) alkylamino, di($C_1$–$C_4$) alkylamino, ($C_1$–$C_4$)hydroxyalkyl-amino, di($C_1$–$C_4$) hydroxyalkylamino, ($C_1$–$C_4$) hydroxyalkyl ($C_1$–$C_4$) alkylamino, pyrrolidino, piperidino, morpholino, phenylamino, nitro, phenyl, phenylazo, phenylmercapto, or benzoyl groups.

4. The radiation-sensitive mixture as claimed in claim 3, wherein the compound a) is substituted with one or more benzoyl groups that are substituted with a ($C_1$–$C_4$) alkyl, ($C_1$–$C_4$) alkoxy, or diazonium group.

5. The radiation-sensitive mixture as claimed in claim 3, wherein the compound a) is substituted with one or more phenylmercapto groups that are substituted with a ($C_1$–$C_4$) alkyl or ($C_1$–$C_4$)alkoxy group.

6. The radiation-sensitive mixture as claimed in claim 1, wherein compound a) is a heteroaromatic compound, wherein the heteroatoms are selected from the group consisting of oxygen, sulfur, and nitrogen.

7. The radiation-sensitive mixture as claimed in claim 1, wherein the compound a) is a di-benzofuran-x-diazonium 1,1,2,3,3,3-hexafluoropropanesulfonate, a di-benzo(b,d)-thiophene-x-diazonium 1,1,2,3,3,3-hexafluoropropane-sulfonate, or a 9-($C_1$–$C_4$)alkyl-carbazole-x-diazonium 1,1, 2,3,3,3-hexafluoropropanesulfonate, where x specifies the position number.

8. The radiation-sensitive mixture as claimed in claim 1, wherein the proportion of diazonium salt is from about 1 to about 40 percent by weight based on the total weight of the nonvolatile constituents of the mixture.

9. The radiation-sensitive mixture as claimed in claim 1, which comprises a compound $b^1$), wherein compound $b^1$) is a polymer containing acid-labile groups.

10. The radiation-sensitive mixture as claimed in claim 9, wherein the polymer containing acid-labile groups is a polymer containing at least one acid-cleavable C—O—C bond.

11. The radiation-sensitive mixture as claimed in claim 9, wherein the polymer contains aromatic rings which are substituted with acid-cleavable tert-butoxycarbonyloxy, tert-butoxycarbonyl or tert-butoxy groups.

12. The radiation-sensitive mixture as claimed in claim 1, which comprises a compound $b^1$), wherein the compound $b^1$) is an o-quinone diazide.

13. The radiation-sensitive mixture as claimed in claim 12, wherein the o-quinone diazide is an o-naphthoquinone diazide.

14. The radiation-sensitive mixture as claimed in claim 13, wherein the o-naphthoquinone diazide is an ester of (1,2-naphthoquinone 2-diazide)-4- or -5-sulfonic acid and a compound containing phenolic hydroxyl groups.

15. The radiation-sensitive mixture as claimed in claim 14, wherein the compound containing phenolic hydroxy groups contains 2 to 6 phenolic hydroxyl groups.

16. The radiation-sensitive mixture as claimed in claim 1, wherein compound $b^2$) is present, and the compound $b^2$) contains at least two acid-crosslinkable groups.

17. The radiation-sensitive mixture as claimed in claim 16, wherein the acid-crosslinkable groups are selected from the group consisting of hydroxymethyl, alkoxymethyl, and oxiranylmethyl groups.

18. The radiation-sensitive mixture as claimed in claim 17, wherein the compound $b^2$) is a melamine/formaldehyde or urea/formaldehyde condensate containing at least two N-hydroxymethyl, N-alkoxymethyl or N-acyloxymethyl groups.

19. The radiation-sensitive mixture as claimed in claim 1, which additionally comprises a polymeric organic binder which is insoluble in water but soluble, or at least swellable, in aqueous alkaline solution.

20. The radiation-sensitive mixture as claimed in claim 19, wherein the binder c) is a polymer containing phenolic hydroxyl groups or carboxyl groups.

21. The radiation-sensitive mixture as claimed in claim 20, wherein the polymer is a novolak or a polyhydroxystyrene.

22. A recording material having a base and a radiation-sensitive coating, wherein the coating is composed of a radiation-sensitive mixture as claimed in claim 1.

* * * * *

UNITED STATES PATENT AND TRADEMARK OFFICE
CERTIFICATE OF CORRECTION

PATENT NO.   : 5,776,652
DATED        : July 7, 1998
INVENTOR(S)  : Mathias EICHHORN et al.

It is certified that error appears in the above-identified patent and that said Letters Patent is hereby corrected as shown below:

Column 9, line 40, contains a typographical error wherein "EXAMPLLE 10 TO 19" should read --EXAMPLES 10 TO 19-- and Column 9, TABLE 2, line 60, delete "$CF_3CHFC_2SO_3^-$" and insert --$CF_3CHFCF_2SO_3^-$--.

Signed and Sealed this

Twenty-ninth Day of June, 1999

Attest:

Q. TODD DICKINSON

*Attesting Officer*  *Acting Commissioner of Patents and Trademarks*